(12) United States Patent
Zhai et al.

(10) Patent No.: US 11,628,192 B2
(45) Date of Patent: Apr. 18, 2023

(54) BACTEROIDES FRAGILIS FOR RELIEVING ENDOTOXIN INFECTION AND APPLICATION THEREOF

(71) Applicant: Jiangnan University, Wuxi (CN)

(72) Inventors: Qixiao Zhai, Wuxi (CN); Wei Chen, Wuxi (CN); Huizi Tan, Wuxi (CN); Wenwei Lu, Wuxi (CN); Fengwei Tian, Wuxi (CN); Jianxin Zhao, Wuxi (CN); Hao Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 183 days.

(21) Appl. No.: 17/082,668

(22) Filed: Oct. 28, 2020

(65) Prior Publication Data

US 2021/0038655 A1 Feb. 11, 2021

Related U.S. Application Data

(63) Continuation of application No. PCT/CN2018/110059, filed on Oct. 12, 2018.

(30) Foreign Application Priority Data

Apr. 28, 2018 (CN) .......................... 201810397388.1

(51) Int. Cl.
*A01N 63/00* (2020.01)
*A61K 35/741* (2015.01)
*A61P 31/04* (2006.01)
*A61P 1/00* (2006.01)
*A61K 9/20* (2006.01)
*A61K 35/00* (2006.01)

(52) U.S. Cl.
CPC .......... *A61K 35/741* (2013.01); *A61K 9/2009* (2013.01); *A61K 9/2018* (2013.01); *A61K 9/2054* (2013.01); *A61K 9/2059* (2013.01); *A61P 1/00* (2018.01); *A61P 31/04* (2018.01); *A61K 2035/115* (2013.01)

(58) Field of Classification Search
None
See application file for complete search history.

(56) References Cited

U.S. PATENT DOCUMENTS

2004/0219587 A1* 11/2004 Bennett-Guerrero ....................... A61K 39/0275
435/6.16

FOREIGN PATENT DOCUMENTS

| CN | 106399141 A | 2/2017 |
| CN | 108611295 A | 10/2018 |

OTHER PUBLICATIONS

FujiFilm Chemicals USA corporation, Published on Dec. 10, 2015). (Year: 2015).*
Elaine. Y.H. et al. "The Microbiota Modulates Gut Physiology and Behavioral Abnormalities Associated with Autism" Cell., vol. 155. No. (7). Dec. 19, 2013 (Dec. 19, 2013).
Feng. Shuzhen et al. The Research Progress of Bacteroides Fragilis. (Microbiology), vol. 42. No. (7). Jul. 20, 2015 (Jul. 20, 2015).
Zhang. Jijie et al. Non-official translation: Isolation and Identification of Non-toxic Bacteroides Fragilis. Ningxia Medical Journal), vol. 13, No. (4), Apr. 30, 1991 (Apr. 30, 1991).
Zhang, Jijie et al.). "Clinical Application of Bacteroides Fragilis (BF839) Fluid" Chinese Journal of Biologicals, vol. 8, No. (2), Feb. 28, 1995 (Feb. 28, 1995).

* cited by examiner

*Primary Examiner* — Jana A Hines
*Assistant Examiner* — Khatol S Shahnan Shah
(74) *Attorney, Agent, or Firm* — IPro, PLLC; Na Xu

(57) ABSTRACT

The disclosure discloses *Bacteroides fragilis* for relieving endotoxin infection and application thereof, and belongs to the technical field of microorganisms. The *Bacteroides fragilis* CCFM1020 of the disclosure has low immunogenicity, and can reduce the content of pro-inflammatory factors and increase the concentration of anti-inflammatory factors in the blood of hosts infected with endotoxin, up-regulate the number of Foxp3$^+$ regulatory T cells and stabilize the composition of the intestinal microbiota. A pharmaceutical composition of the *Bacteroides fragilis* CCFM1020 for relieving endotoxin infection has broad application prospects.

10 Claims, 4 Drawing Sheets

BACTEROIDES FRAGILIS FOR RELIEVING ENDOTOXIN INFECTION AND APPLICATION THEREOF

TECHNICAL FIELD

The disclosure relates to *Bacteroides fragilis* for relieving endotoxin infection and application thereof, and belongs to the technical field of microorganisms.

BACKGROUND

Endotoxin, also known as lipopolysaccharide, is an important component of the cell wall of Gram-negative bacteria. Endotoxin has a stable structure, and is mainly composed of polysaccharide O antigen, core polysaccharides and lipid A. Lipid A is lipidated glucosamine with pyrogenic effects, and is the toxic component of endotoxin from Gram-negative bacteria. Normally, endotoxin will be released only when the bacteria is dead and lysed or the bacterial cells are destroyed by artificial treatments. However, endotoxin has a stable structure, and cannot be inactivated unless under long-term high-temperature treatment and/or assisted by strong alkali, acid or oxidant.

Healthy mammalian intestine is colonized by a large number of commensal bacteria The intestinal mucosa can selectively absorb nutrients and prevent the entry of microorganisms and their harmful metabolites. However, when the body is under stress or overuses antibiotics, the intestinal microbiota will be disturbed and endotoxin will be released. Excessive endotoxin can increase the intestinal permeability, cause a series of intestinal diseases mediated by immune disorders; give rise to microcirculation disorder and endotoxic shock by entering the blood circulation through the barrier, and attacking macrophages, neutrophils, endothelial cells, platelets, the complement system and the coagulation system; and possibly aggravate depression. Studies have reported that at least 750,000 patients are suffering from endotoxin infection shock each year, among which more than 210,000 people die.

Generally, the treatments for endotoxin infection are mostly designed to reduce the production and promote the absorption of endotoxin and improve microcirculation disorder caused by endotoxin. Traditional Chinese medicine treatments have certain effects on the elimination of endotoxin, but the effects are not significant or stable. Applications of antibiotics cannot effectively remove endotoxin, but introduce negative effects. Blood purification may be effective, but the cost is relatively high with insufficient clinical data.

Therefore, to regulate the intestinal microbiota has broad application prospects in the treatment or prevention of endotoxin infection.

SUMMARY

The disclosure provides a novel strain of *Bacteroides fragilis*, which is named *Bacteroides fragilis* CCFM1020. The bacteria was identified as *Bacteroides fragilis* CCFM1020 according to the gene sequence, and has been preserved at the Guangdong Microbial Culture Collection Centeron Mar. 29, 2018, with the preservation address of $5^{th}$ Floor, Building 59, Courtyard 100, Xianlie Middle Road, Guangzhou, and the preservation number of GDMCC No: 60342.

The *Bacteroides fragilis* CCFM1020 used the original number HCK-B3 before being submitted to the Guangdong Microbial Culture Collection Center, that is, the numbers CCFM1020 and HCK-B3 represent the same strain of *Bacteroides fragilis*.

The *Bacteroides fragilis* CCFM1020 has the following properties of:

1) having low immunogenicity and no significant effects on immune factors in the blood and colon tissues of mice;

2) being capable of reducing the content of pro-inflammatory factors and increasing the concentration of anti-inflammatory factors in the blood of mice infected with endotoxin;

3) being capable of up-regulating the number of $Foxp3^+$ regulatory T cells in the spleen of mice infected with endotoxin; and 4) being capable of stabilizing the intestinal microbiota composition of mice infected with endotoxin.

Bacteria characteristics: the bacteria are Gram-negative and rod-shaped, are arranged individually or in pairs, are about 0.9-1.2 µm wide and 3-8 µm long, and have no sporulation.

Bacterial colony characteristics: obvious colonies are formed on a culture medium with the diameter of 1-3 mm; the front morphology is circle; the side morphology is convex; the edges are neat, the colonies are transparent or translucent; and the surface is moist and smooth.

Growth characteristics: the strain is strictly anaerobic, is sensitive to oxygen, and can grow nicely under the temperature of 30-37° C. and the pH between 8.0 and 5.0. The most suitable pH for growth is 7.0.

The disclosure further provides application of the *Bacteroides fragilis* CCFM1020 in preparing a pharmaceutical composition for relieving endotoxin infection.

In one embodiment, the pharmaceutical composition is composed of bacterial agents of *Bacteroides fragilis* CCFM1020 and pharmaceutically acceptable carriers.

In one embodiment, the composition further contains a cytoprotective agent.

In one embodiment, the cytoprotective agent includes but is not limited to a phosphate buffer solution.

In one embodiment, the pharmaceutically acceptable carriers include one or more carriers selected from those commonly used in pharmacy as fillers, binders, wetting agents, disintegrants, lubricants and flavoring agents.

In one embodiment, the pharmaceutical composition is in the form of granules, capsules, tablets, pills or oral liquid.

In one embodiment, the percentage of the *Bacteroides fragilis* CCFM1020 in the pharmaceutical composition is 15-35% or 20-30% by weight.

In one embodiment, the fillers refer to excipient diluents used for increasing the weight and volume of tablets to facilitate compressing, or excipient absorbents for absorbing excess liquid components in the raw materials. The fillers can be selected from starch, sucrose, lactose, calcium sulfate or microcrystalline cellulose.

In one embodiment, the binders refer to viscous substances that can be added when the drug has no viscosity or insufficient viscosity so as to facilitate granulation. The binders can be selected from cellulose derivatives, alginate, gelatin or polyvinylpyrrolidone.

In one embodiment, the wetting agents refer to liquid that can be added when the drug has no viscosity, so as to wet the raw materials and excipients of the drug to induce the viscosity and form granules. The wetting agents can be selected from water, ethanol, starch or syrup.

In one embodiment, the disintegrants refer to excipients that can be added to tablets to promote rapid disintegration into fine particles in the gastrointestinal fluid. The disintegrants can be selected from sodium carboxymethyl starch, hydroxypropyl cellulose, croscarmellose, agar, calcium carbonate or sodium bicarbonate.

In one embodiment, the lubricants refer to chemical substances that can improve the mobility of tablets during processing and demoulding. The lubricants can be selected from talc, calcium stearate, magnesium stearate, superfine silica gel powder or polyethylene glycol.

In one embodiment, the flavoring agents refer to excipients used in drugs to improve or shield the undesirable smell and taste. The flavoring agents can be selected from sweeteners such as simple syrup, sucrose, lecithin, orange syrup or cherry syrup; aromatics such as lemon, fennel or peppermint oil; mucilage agents such as sodium alginate, gum arabic, gelatin, methyl cellulose or sodium carboxymethyl cellulose; and effervescingagents such as citric acid, tartaric acid or a mixture of sodium bicarbonate.

In one embodiment, the pharmaceutical composition can be presented in the form of granules, capsules, tablets, pills or oral liquid. Each single form contains predetermined active substances in sufficient amount, for example, the bacterial agent of *Bacteroides fragilis* CCFM1020 of the disclosure.

The disclosure further provides a bacterial agent of *Bacteroides fragilis* CCFM1020, containing the *Bacteroides fragilis* CCFM1020 and cytoprotective agents.

In one embodiment, the cytoprotective agent includes a sodium alginate solution.

In one embodiment, the cytoprotective agent includes starch, cellulose derivatives, sodium carboxymethyl starch, talc, a sucrose water solution or a mixture thereof.

In one embodiment, the bacterial agent is powder obtained by preparing bacterial liquid containing the *Bacteroides fragilis* CCFM1020 through a conventional freeze-drying process or other processes, and contains active *Bacteroides fragilis* CCFM1020 cells with the content of $10^6$ CFU/g or above.

In one embodiment, the bacterial agent of *Bacteroides fragilis* CCFM1020 contains active *Bacteroides fragilis* CCFM1020 with the content of at least $10^6$ CFU/g.

The disclosure further provides a method for culturing the *Bacteroides fragilis* CCFM1020, including inoculating the *Bacteroides fragilis* CCFM1020 into culture medium and anaerobically culturing at 35-37° C.

In one embodiment of the disclosure, the strain is cultured for 12-18 h to reach a stationary phase.

In one embodiment of the disclosure, a BHI culture medium is used for culture.

In one embodiment of the disclosure, cysteine hydrochloride (1 g/L), hemin (0.01 g/L), and vitamin K1 (0.002 g/L) are also added to the BHI culture medium.

The disclosure further provides a cryopreserved agent of *Bacteroides fragilis*, containing the *Bacteroides fragilis* CCFM1020 with the content of greater than or equal to $10^{10}$ CFU/mL.

In one embodiment of the disclosure, the cryopreserved agent is prepared by washing the bacterial liquid of *Bacteroides fragilis* CCFM1020 in a stationary phase with a phosphate buffer solution of pH 7.0-7.2 for 1-2 times, adding a protective agent and carrying out preservation at −80° C. for later use.

In one embodiment of the disclosure, the protective agent contains cysteine hydrochloride (1 g/L) and glycerol (200 g/L).

The disclosure further provides application of the *Bacteroides fragilis* in relieving endotoxin infection, and the application is to ingest the *Bacteroides fragilis* or a composition containing the *Bacteroides fragilis* into the body.

In one embodiment, the *Bacteroides fragilis* is ingested into the body in the form of a pharmaceutical composition.

Beneficial effects: The *Bacteroides fragilis* CCFM1020 of the disclosure has low immunogenicity, can significantly improve the serum content of inflammatory factors and the number of Foxp3$^+$ regulatory T cells in the spleen of the mice infected with endotoxin to the level of normal mice, and can stabilize the composition of the intestinal microbiota of mice infected with endotoxin. The *Bacteroides fragilis* CCFM1020 can be used to prepare a pharmaceutical composition that are capable of relieving endotoxin infection, and has broad application prospects.

PRESERVATION PROOF OF THE BIOLOGICAL MATERIALS

Figure 1:
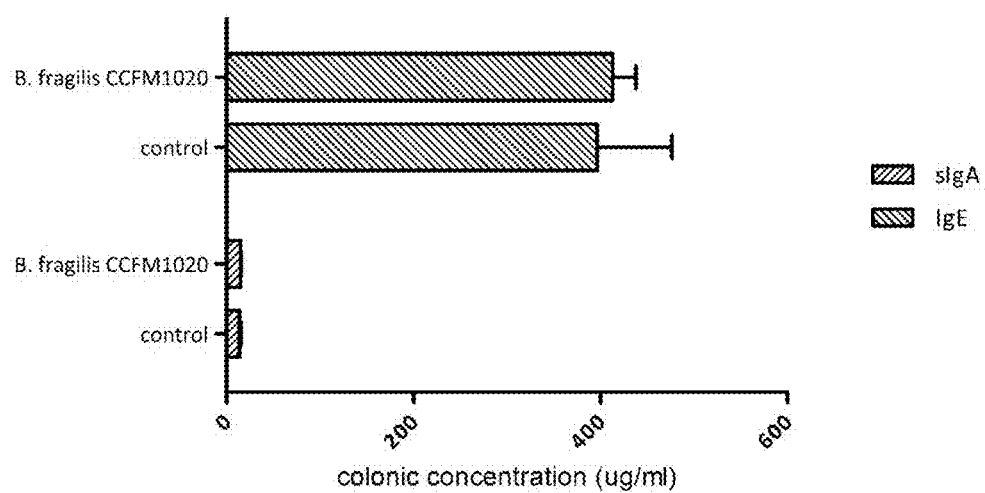
FIG. 1 shows the concentration of immune factors in the blood and colon tissues of mice after intragastric administration of *Bacteroides fragilis* CCFM1020.

A novel *Bacteroides* strain, with a taxonomic name of *Bacteroides fragilis*, has been preserved at the Guangdong Microbial Culture Collection Center on Mar. 29, 2018, with the preservation address of 5th Floor, Building 59, Courtyard 100, Xianlie Middle Road, Guangzhou, and the preservation number of GDMCC No: 60342.

DETAILED DESCRIPTION

Example 1: Culture and Preservation of *Bacteroides fragilis* CCFM1020

1. Preparation of a culture medium: brain heart infusion BHI culture medium (such as a product of Qingdao Haibo Biotechnology Co., Ltd.) was prepared in distilled water. Cysteine hydrochloride (1 g/L), hemin (0.01 g/L) and vitamin K1 (0.002 g/L) were added and mixed uniformly. The pH was adjusted to 7.0, and sterilization was carried out at 115-121° C. for 15-20 min to obtain the culture medium.

2. Culture method: *Bacteroides fragilis* CCFM1020 was inoculated according to an inoculation amount of 2-4% based on the weight of the above culture medium, and anaerobically cultured at 37° C. for 12-18 h to reach a stationary phase.

3. Preparation of protective agent: cysteine hydrochloride (1 g/L) and glycerol (200 g/L) were weighed and uniformly dissolved in distilled water, and the mixed solution was sterilized at 115-121° C. for 15-20 min to obtain the protective agent.

4. Preservation method: liquid culture of *Bacteroides fragilis* CCFM1020 in the stationary phase was washed with a sterile phosphate buffer solution (pH 7.2) for 1-2 times, and then resuspend with the protective agent to reach the concentration of $10^{10}$ CFU/mL, so as to obtain the *Bacteroides fragilis* CCFM1020 cryopreserved agent, and the *Bacteroides fragilis* CCFM1020 cryopreserved agent was preserved at −80° C. for later use.

Example 2: Tolerance Dose Experiment in Mice with Intragastric Administration of *Bacteroides fragilis* CCFM1020

10 of 6-8 week old healthy female C57BL6 mice intragastrically administered with 0.1 mL of the cryopreserved agent of *Bacteroides fragilis* CCFM1020 ($10^{10}$ CFU/mL) prepared as Example 1 once every 24 hours. The mice were observed for 5 days and the body weight and death of the mice were recorded.

Results are shown in Table 1, which indicated that feeding the *Bacteroides fragilis* CCFM1020 at the concentration of $10^9$ CFU did not cause any negative effects on the mice. The mice grew normally, no death occurred, and the mice had no pathological symptoms.

TABLE 1

Influence of $10^9$ CFU of *Bacteroides fragilis* CCFM1020 on the body weight of mice

| Time (d) | 1 | 2 | 3 | 4 | 5 |
|---|---|---|---|---|---|
| Body weight (g) | 20.49 ± 0.53 | 20.92 ± 0.77 | 21.20 ± 0.53 | 21.49 ± 0.68 | 21.77 ± 0.36 |
| Death | None | None | None | None | None |

Example 3: Immune Tolerance Experiment in Mice with Intragastric Administration of *Bacteroides fragilis* CCFM1020

20 of 6-8 week old healthy female C57BL6 mice were randomly divided into two groups: a negative control group and a *Bacteroides fragilis* CCFM1020 intervention group, each group contained 10 mice. Mice in the *Bacteroides fragilis* CCFM1020 intervention group were intragastrically administered with 0.1 mL of the above *Bacteroides fragilis* CCFM1020 cryopreserved agent ($10^{10}$ CFU/mL) once every 24 hours, while mice in the control group were intragastrically administered with 0.1 mL of the protective agent of the above cryopreserved agent once every 24 hours. All mice were sacrificed after 5 days of continuous intragastric administration. After blood and colon tissue were taken, lysed and homogenized with RIPA lysate (a product of Beyotime Biotechnology Co., Ltd.), the concentration of immune factors was determined with an ELISA kit (a product of Nanjing SenBeiJia Biological Technology Co., Ltd.).

Experimental results are shown in FIG. 1, which indicated that the contents of the immune factors of TNF-α, IL-6, IL-10 and CXCL-2 in the blood and the immune factors of sIgA and IgE in the colon tissues of mice in the *Bacteroides fragilis* CCFM1020 intervention group were not significantly different from those of mice in the control group. Therefore, the results of Example 3 show that *Bacteroides fragilis* CCFM1020 of the disclosure does not stimulate the immune system of mice and has low immunogenicity.

Example 4: Regulating Effects of *Bacteroides fragilis* CCFM1020 on the Level of Immune Factors in the Blood of Mice Infected with Endotoxin 30 of 6-8 week old healthy female C57BL6 mice were randomly divided into three groups: a negative control group, an endotoxin infection model group and a *Bacteroides fragilis* CCFM1020 treatment group, each group contained 10 mice. Mice in the endotoxin infection group and the *Bacteroides fragilis* CCFM1020 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent prepared in Example 1 once every 24 hours. The mice in the *Bacteroides fragilis* CCFM1020 treatment group were intragastrically administered with 0.1 mL of the *Bacteroides fragilis* CCFM1020 cryopreserved agent ($10^{10}$ CFU/mL) prepared in Example 1 once every 24 hours. All mice were sacrificed after 5 consecutive days. Blood was collected and the concentration of immune factors was determined by using an ELISA kit (a product of Nanjing SenBeiJia Biological Technology Co., Ltd.).

Figure 2:
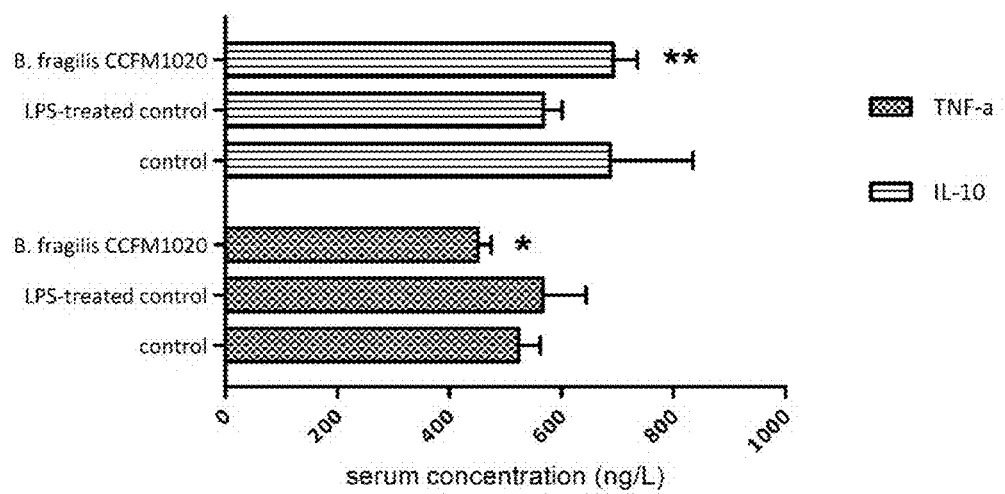
FIG. 2 shows the regulating effects of *Bacteroides fragilis* CCFM1020 on the level of immune factors in the blood of mice infected with endotoxin; * indicates that there is a significant difference between the *Bacteroides fragilis* CCFM1020 group and the endotoxin model group, * indicates $p<0.05$, and ** indicates $p<0.01$.

Experimental results are shown in FIG. 2, which indicated that endotoxin infection increased the content of the pro-inflammatory factor TNF-α in the blood of mice from 522.93 ng/L to 566 ng/L, while decreased the anti-inflammatory factor IL-10 from 686.83 ng/L to 567.68 ng/L. After treatment with *Bacteroides fragilis* CCFM1020, the content of TNF-α in the blood of mice was significantly reduced to 450 ng/L (p<0.05), and the content of IL-10 was increased to 692 ng/L (p<0.01), making the levels of the above immune factors approaching those of normal mice. The above results indicate that *Bacteroides fragilis* CCFM1020 of the disclosure can relieve the inflammatory response caused by endotoxin infection.

Example 5: Regulating Effects of *Bacteroides fragilis* CCFM1020 on the Content of Regulatory T Cells in the Spleen of Mice Infected with Endotoxin 30 of 6-8 week old healthy female C57BL6 mice were randomly divided into three groups: a negative control group, an endotoxin infection model group and a *Bacteroides fragilis* CCFM1020 treatment group, each group contained 10 mice. Mice in the endotoxin infection group and the *Bacteroides fragilis* CCFM1020 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent once every 24 hours. The mice in the *Bacteroides fragilis* CCFM1020 treatment group were intragastrically administered with 0.1 mL of the *Bacteroides fragilis* CCFM1020 cryopreserved agent ($10^{10}$ CFU/mL) once every 24 hours. All mice were sacrificed after 5 consecutive days. After the spleen tissue was taken, lysed and homogenized with red blood cell lysate, CD4, CD25 and surface molecule Foxp3 were labeled by using a mouse regulatory T cell staining kit (a product of eBioscience company), and the levels of the regulatory T cells was detected by flow cytometry (FACSCalibur, BD company).

Figure 3:
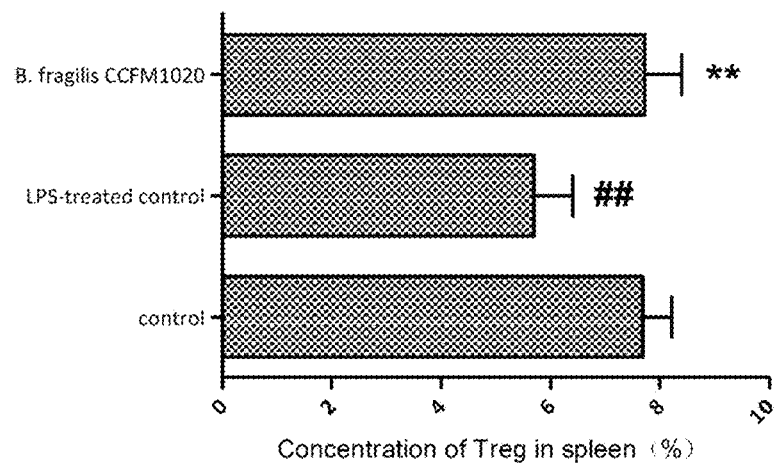
FIG. 3 shows the regulating effects of *Bacteroides fragilis* CCFM1020 on the level of regulatory T cells in the spleen of mice infected with endotoxin; * indicates that there is a significant difference between the *Bacteroides fragilis* CCFM1020 group and the endotoxin model group, and ** indicates $p<0.01$; # indicates that there is a significant difference between the endotoxin infection group and the control group, and ## indicates $p<0.01$.
Figure 4:
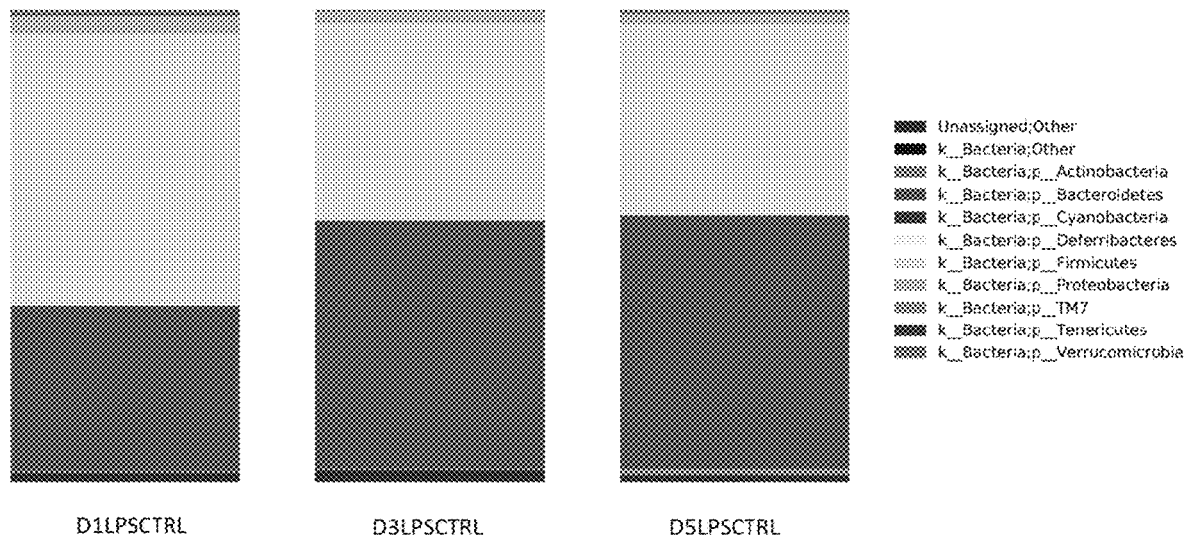
FIG. 4 shows the intestinal microbiota of mice in the endotoxin infection group; D1LPSCTRL: the intestinal microbiota of mice in the endotoxin infection group on the 1st day of the experiment; D3LPSCTRL: the intestinal microbiota of mice in the endotoxin infection group on the 3rd day of the experiment; and D5LPSCTRL: the intestinal microbiota of the mice in the endotoxin infection group on the 5th day of the experiment.
Figure 5:
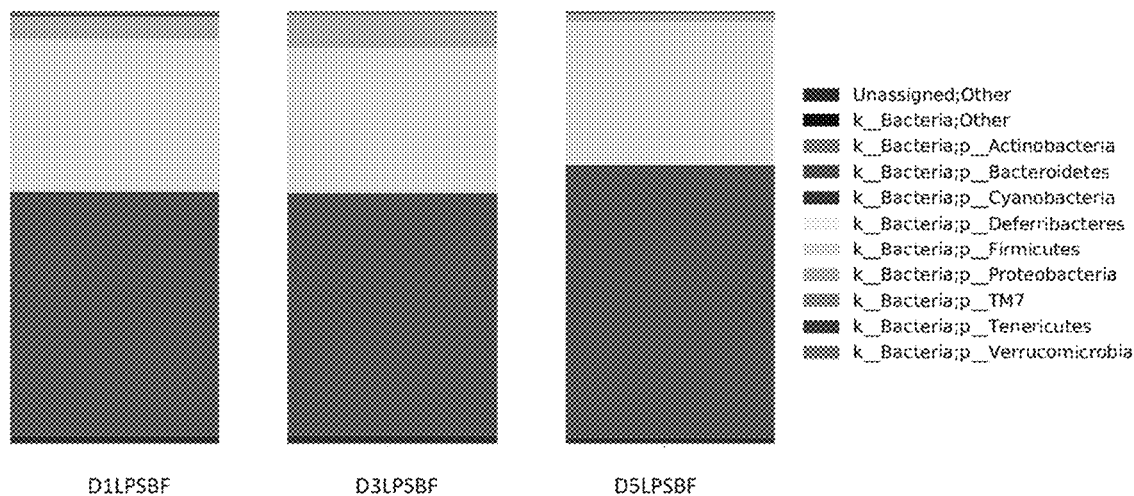
FIG. 5 shows the regulating effects of *Bacteroides fragilis* CCFM1020 on the composition of the intestinal microbiota of mice infected with endotoxin; D1LPSBF: the intestinal microbiota of mice in the endotoxin infection group with the intervention of *Bacteroides fragilis* CCFM1020 on the 1st day of the experiment; D3LPSBF: the intestinal microbiota of mice in the endotoxin infection group with the intervention of *Bacteroides fragilis* CCFM1020 on the 3rd day of the experiment; and D5LPSBF: the intestinal microbiota of mice in the endotoxin infection group with the intervention of *Bacteroides fragilis* CCFM1020 on the 5th day of the experiment.
Figure 6:
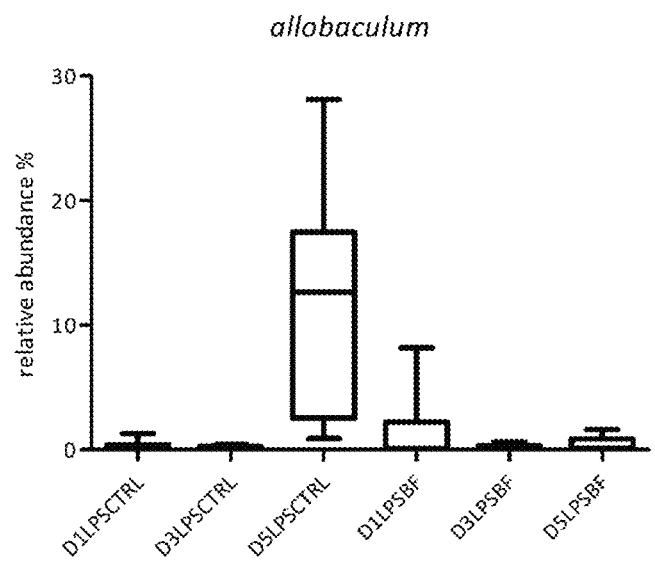
FIG. 6 shows the relative abundance of *Allobaculum* in the intestinal microbiota of mice infected with endotoxin and in the intestinal microbiota of mice in the endotoxin infection group with the intervention of *Bacteroides fragilis* CCFM1020.
Figure 7:
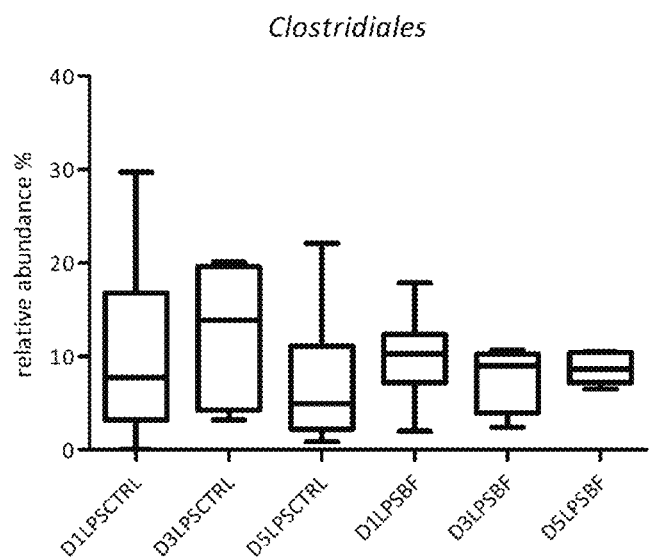
FIG. 7 shows the relative abundance of *Clostridiales* in the intestinal microbiota of mice infected with endotoxin and in the intestinal microbiota of mice in the endotoxin infection group with the intervention of *Bacteroides fragilis* CCFM1020.
Figure 8:
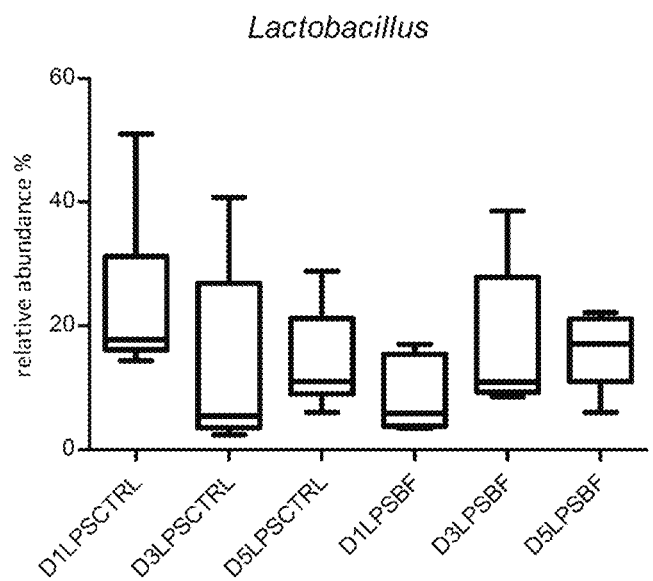
FIG. 8 shows the relative abundance of *Lactobacillus* in the intestinal microbiota of mice infected with endotoxin and in the intestinal microbiota of mice in the endotoxin infection group with the intervention of *Bacteroides fragilis* CCFM1020.

Experimental results are shown in FIG. 3, which indicated that endotoxin infection significantly reduced the Foxp3$^+$ regulatory T cells in the spleen of mice from 7.69% to 5.69% (p<0.01). After treatment with *Bacteroides fragilis* CCFM1020, the content of the regulatory T cells in the spleen of mice increased significantly to 7.73% (p<0.01), which was close to the level of mice in the control group. The results of Example 5 indicate that the *Bacteroides fragilis* CCFM1020 of the disclosure can relieve the inflammatory response caused by endotoxin infection.

Example 6: Regulating Effects of *Bacteroides fragilis* CCFM1020 on the Composition of the Intestinal Microbiota of Mice Infected with Endotoxin 30 of 6-8 week old healthy female C57BL6 mice were randomly divided into three groups: a negative control group, an endotoxin infection model group and a *Bacteroides fragilis* CCFM1020 treatment group, each group contained 10 mice. Mice in the endotoxin infection group and the *Bacteroides fragilis* CCFM1020 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent once every 24 hours. The mice in the *Bacteroides fragilis* CCFM1020 treatment group were intragastrically administered with 0.1 mL of the *Bacteroides fragilis* CCFM1020 cryopreserved agent ($10^{10}$ CFU/mL) once every 24 hours. All mice were sacrificed after 5 consecutive days. During the experiment, the mouse feces was taken before intragastric administration on the first day and after intragastric administration on the third day and the fifth day. After extracting the genomic DNA of fecal bacteria with a Fast DNA Spin Kit for Feces (a product of MP Biomedicals Company), the 16s V3-V4 region sequence was amplified by PCR, and the differences in the composition of the intestinal microbiota in the feces samples were determined by next-generation sequencing.

Experimental results are shown in FIGS. 4 to 8. The abundance of Bacteroidetes and Firmicutes in the intestines of mice infected with endotoxin were 50% and 40% respectively, wherein *Bacteroides* S24-7 accounted for 42.7%, *Lactobacillus* accounted for 12%, *Clostridiales* accounted for 8.2%, and the content of *Allobaculum* related to colitis increased significantly to 10%, with a decrease in the diversity of intestinal microbiota. After treatment with *Bacteroides fragilis* CCFM1020, it was found that the abundance of Bacteroidetes and Firmicutes in the fecal microbiota of mice were adjusted to 60% and 30% respectively, wherein the variations of *Bacteroides, Clostridiales* and *Allobaculum* were greatly reduced, the abundance of which was 38.3%, 8.7% and 0.5% respectively, and the content of *Lactobacillus* increased to about 15%. Therefore, the results of Example 6 showed that the *Bacteroides fragilis* CCFM1020 of the disclosure can improve the disorders of the intestinal microbiota caused by LPS, increase the diversity of the intestinal microbiota and stabilize the balance of the intestinal microbiota, thereby prevent a series of diseases that may be caused by the imbalance of the intestinal microbiota caused by endotoxin.

The above examples showed that the *Bacteroides fragilis* CCFM1020 of the disclosure can help relieve the imbalance of the composition of the intestinal microbiota and the immune response caused by endotoxin infection in mice.

Example 7: Preparation of Capsule Products Containing *Bacteroides fragilis* CCFM1020 of the Disclosure The *Bacteroides fragilis* CCFM1020 of the disclosure was cultured anaerobically in BHI culture medium at 37° C. for 24 hours. The liquid culture was centrifuged at 5000 rpm for 15 min at 4° C., and washed 1-2 times with a sterile phosphate buffer solution (pH 7.2). The bacteria were resuspended using the above protective agent to make the final concentration of the bacteria reach $10^{10}$ CFU/mL. The bacterial suspension was added to sodium alginate solution, and mixed thoroughly to make cells evenly dispersed. Then the mixed solution was squeezed into a calcium chloride solution to form colloidal particles. After static solidification for 30 min, the colloidal particles were filtered and collected. The collected colloidal particles were freeze-dried for 48 hours to obtain powder containing the *Bacteroides fragilis* CCFM1020 of the disclosure. The powder was encapsulated with commercially available medicinal capsules to obtain the capsule product.

Example 8: Preparation of Tablets Using *Bacteroides fragilis* CCFM1020 of the Disclosure 25.7 parts by weight of the *Bacteroides fragilis* CCFM1020 bacterial powder preparation of the disclosure prepared by a freeze-drying method, 55.0 parts by weight of starch, 4.5 parts by weight of a cellulose derivative, 12.0 parts by weight of sodium carboxymethyl starch, 0.8 part by weight of talc, 1.0 part by weight of sucrose and 1.0 part by weight of water were individually weighed and mixed. The mixed material was made into wet granules by a conventional method, and then the wet granules were compressed with a tablet press produced by Zhongnan Pharmaceutical Machinery. The tablets were dried by a small medicine dryer produced by Qingzhou Yikang Traditional Chinese Medicine Machinery Co., Ltd., and then the tablets were packaged to obtain the tablets of the disclosure.

Although the disclosure has been disclosed as above in preferred examples, it is not intended to limit the disclosure. Without departing from the spirit and scope of the disclosure, anyone familiar with this technology can make various changes and modifications. Therefore, the protection scope of the disclosure should be defined by the claims.

What is claimed is:

1. A composition comprising:
    a bacterium of *Bacteroides fragilis* with a preservation number of GDMCC No: 60342, preserved at the Guangdong Microbial Culture Collection Center (GDMCC) on Mar. 29, 2018,
    a cryoprotective agent, wherein the cytoprotective agent comprises a phosphate buffer solution, and
    a powder cryopreserve agent,
    wherein active *Bacteroides fragilis* is present in the composition at $10^6$ CFU/g or higher.

2. The composition of claim 1, further comprising a pharmaceutically acceptable carrier.

3. The composition of claim 2, wherein the pharmaceutically acceptable carrier comprises one or more fillers, binders, wetting agents, disintegrants, lubricants, and flavoring agents.

4. The composition of claim 3, wherein the fillers comprise excipient diluents or excipient absorbents.

5. The composition of claim 3, wherein the binders are viscous substances that are added to a drug when the drug has no viscosity or insufficient viscosity, so as to facilitate granulation.

6. The composition of claim 3, wherein the wetting agents are liquid that are added to a drug when the drug has no viscosity.

7. The composition of claim 3, wherein the disintegrants are excipients that are added to tablets to promote rapid disintegration into fine particles in gastrointestinal fluid.

8. The composition of claim 3, wherein the lubricants are chemical substances that improve the mobility of tablets during processing and demoulding; and the flavoring agents are excipients used in drugs to improve or shield the undesirable smell and taste.

9. The composition of claim 3, wherein the pharmaceutical composition is in a form of granules, capsules, tablets, pills or oral liquid.

10. A method of regulating intestinal microbiota in a subject in need thereof, which comprises administering to the subject a pharmaceutically effective amount of the composition of claim 1, wherein the subject is suffering from an endotoxin infection.

* * * * *